US008700167B2

(12) United States Patent
Sabel (10) Patent No.: US 8,700,167 B2
(45) Date of Patent: Apr. 15, 2014

(54) APPARATUS AND METHOD FOR STIMULATING A BRAIN OF A PERSON (75) Inventor: Bernhard A. Sabel, Berlin (DE)

(73) Assignee: EBS Technologies GmbH, Kleinmachnow (DE)

( * ) Notice: Subject to any disclaimer, the term of this patent is extended or adjusted under 35 U.S.C. 154(b) by 670 days.

(21) Appl. No.: 12/520,616

(22) PCT Filed: Dec. 22, 2006

(86) PCT No.: PCT/EP2006/070198
§ 371 (c)(1),
(2), (4) Date: Sep. 4, 2009

(87) PCT Pub. No.: WO2008/077440
PCT Pub. Date: Jul. 3, 2008

(65) Prior Publication Data
US 2009/0319004 A1 Dec. 24, 2009

(51) Int. Cl.
A61N 1/00 (2006.01)
(52) U.S. Cl.
USPC .......................................... 607/54
(58) Field of Classification Search
USPC ............................ 607/47, 54, 53
See application file for complete search history.

(56) References Cited

U.S. PATENT DOCUMENTS

| 5,241,967 | A | | 9/1993 | Yasushi et al. |
| 5,522,864 | A | | 6/1996 | Wallace et al. |
| 5,782,874 | A | * | 7/1998 | Loos .................. 607/2 |
| 5,944,747 | A | | 8/1999 | Greenberg et al. |
| 5,999,856 | A | * | 12/1999 | Kennedy .................. 607/57 |
| 6,066,163 | A | | 5/2000 | John |
| 6,547,746 | B1 | * | 4/2003 | Marino .................. 600/554 |
| 2004/0131998 | A1 | | 7/2004 | Marom et al. |
| 2005/0004624 | A1 | * | 1/2005 | Gliner et al. .................. 607/54 |

FOREIGN PATENT DOCUMENTS

| WO | WO 92/19172 A1 | 11/1992 |
| WO | WO 03/043690 A1 | 5/2003 |
| WO | WO 2005/000153 A2 | 1/2005 |
| WO | WO 2005/077452 A1 | 8/2005 |

OTHER PUBLICATIONS

Gothe et al., "Changes in Visual Cortex Excitability in Blind Subjects as Demonstrated by Transcranial Magnetic Stimulation," Brain 125:479-490, 2002.
International Search Report for International Application No. PCT/EP2006/070198, dated Aug. 28, 2007.

* cited by examiner

Primary Examiner — Christopher D Koharski
Assistant Examiner — Philip Edwards
(74) Attorney, Agent, or Firm — Gerald T. Bodner (57) ABSTRACT An apparatus for stimulating a brain (3B) of a person (2) comprising a detector (10) for detecting an induced or a spontaneous physiological signal generated by the brain (3B), a control unit (12) being connected to said detector (10) for comparing the detected physiological signal with a criterion to determine an optimal setting of a variable signal parameter, a first signal generator (8) for applying an electrical stimulation signal (EES) to said person (2) and/or at least one second signal generator (9) for applying a sensory stimulation signal (SSS) to a sensory organ (3A) of said person (2), wherein a signal parameter of the stimulation signals (ESS, SSS) are adjusted to the determined optimal setting of said signal parameter.

15 Claims, 8 Drawing Sheets

Visual field chart (VFC)

*Figure 7b*

Visual stimulation pattern

APPARATUS AND METHOD FOR STIMULATING A BRAIN OF A PERSON

Cross Reference to Related Applications

This application is the U.S. National Stage of International Application No. PCT/EP2006/070198, filed Dec. 22, 2006, which is hereby incorporated by reference.

The invention relates to an apparatus and a method for stimulating a brain of a person, in particular via a sensory organ, such as an eye of the person, to restore impaired regions of the sensory organ or areas in the brain that process sensory or other information.

Sensory organs of a person, such as the eyes, the ears or the sense of touch of a person can be impaired or fail completely. Alternatively, brain structures which process information, both sensory and otherwise, may be impaired following damage. In particular eyes or ears of a person can be damaged through external influences such as accidents or by diseases causing an impairment of the respective sensory organ.

Figure 1A:
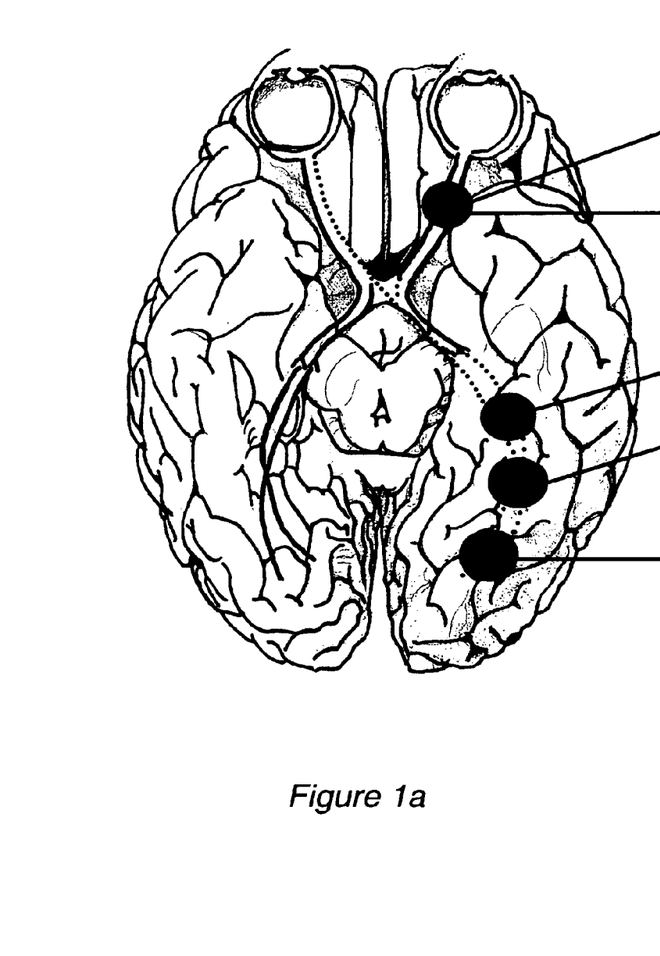
FIGS. 1a, 1b show different types of visual field defects for different types of lesions.
Figure 1B:
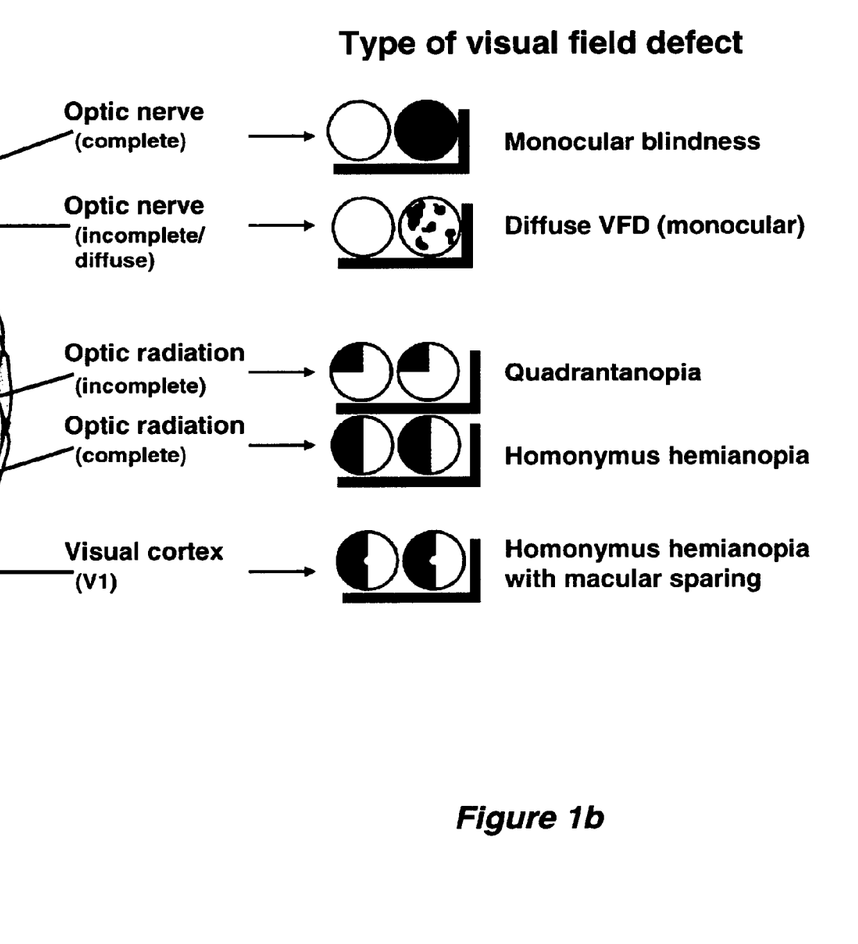

FIGS. 1a, 1b shows as an example of different types of lesions in the visual system of the brain and the corresponding type of visual field defect VFD of a person. For example, a lesion of the optic nerve of one eye causes a monocular blindness on this eye as shown in FIG. 1b. Regions in the visual pathway behind the chiasma, in contrast, result in binocular vision loss. There are many different visual defects which are caused by damage of the retina of the eyes, such as macular degeneration and glaucoma.

In the prior art it is known that stimulation of retina cells can produce phosphenes. U.S. Pat. No. 5,944,747 describes a method of phosphene generation in retina tissues through deeper intermediate retinal cellular electrical stimulation wherein a stimulating electrode is positioned in the vicinity of the retinal tissue and a long duration stimulation signal is applied through an electrode such that deeper intermediate retinal cells are preferentially stimulated over retinal ganglion cells and proximal overlying surface axons.

Also, the brain can be stimulated directly to produce phosphenes. The paper by Gothe et al. (Gothe, J., Brandt, S. A., Irlbacher, K., Röricht, S., Sabel, B. A. and Meyer, B.-U. (2002). Changes in visual cortex excitability in blind subjects as demonstrated by transcranial magnetic stimulation. *Brain* 125: 479-490) describes such an approach.

Further U.S. Pat. No. 5,522,864 describes an apparatus and a method for ocular treatment, wherein a first electrode of a direct current source is placed in direct electrical contact with an eyelid of a person and a second electrode of the current source is placed in direct electrical contact with a skin site of the person so that a direct electrical current can flow between both electrodes at an amplitude of 5-1,000 μAmp for a predetermined period of time to treat defects of the eye.

Thus, the electrical stimulation by applying an electrical signal with variable frequencies to a person via electrodes attached to an eye or to the brain of the person is well known in the prior art. However, in the conventional electrical stimulation methods the electrical stimulation is performed without additional stimulation of the sensory organ such as the eye by a sensory stimulation signal. Furthermore, the adjustments of the signal parameters of the electrical stimulation signal are done by hand in these conventional electrical stimulation methods. Therefore, an application of the electrical stimulation signal is both cumbersome and variable because different operators use different parameter selection criteria. Furthermore, the conventional electrical stimulation of a sensory organ in the conventional electrical stimulation methods is not linked to actual sensory functions. This causes an artificial stimulation to the brain of the person comprising a global electrical stimulation without connection in any meaningful way to functional sensory parameters.

In prior art electrical stimulation methods, the adjustment of the stimulation parameters of the electro-stimulation signal for stimulating a sensory organ is done manually by an operator without taking into account that each individual, i.e. each person, reacts differently to the same electrical stimulation signal. In the conventional electrical stimulation methods the operator has to react to the subjective feedback of the treated person which might indicate whether it does see phosphenes in the treated area of the eye caused by the electrical stimulation signal or not. In response to the information given by the patient the operator will adjust the parameter of the electrical stimulation signal to find a setting which causes an optimal reaction of the patient. For instance, an operator will vary the frequency of a pulsed electrical stimulation signal and ask the treated person to indicate when a maximum amount of phosphenes is caused by the electrical stimulation signal. Naturally a manual adjustment of the frequency of the employed stimulation signals will take some time and will depend strongly on the subjective assessment of the treated person and on the person applying the treatment.

Accordingly, it is an object of the present invention to provide a method and an apparatus which automatically applies optimal stimulation signals to a sensory organ of a person or to the brain of the person according to a selectable and automatically controllable objective criterion.

This object is achieved by an apparatus having the features of main claim 1.

The invention provides an apparatus for stimulating a brain of a person comprising a detector for detecting an induced or a spontaneous physiological signal generated by the brain, a control unit being connected to said detector for comparing the detected physiological signal with a criterion to determine an optimal setting of a variable signal parameter, a first signal generator for applying an electrical stimulation signal to said person and/or at least one second signal generator for applying a sensory stimulation signal to a sensory organ of said person, wherein a signal parameter of the stimulation signals are adjusted to the determined optimal setting of said signal parameter.

In one embodiment of the apparatus according to the present invention, the detected physiological signal is an electroencephalogram (EEG) signal, a magneto-encephalogram signal or a BOLD-signal measured by functional magnetic resonance imaging.

In one embodiment of the apparatus according to the present invention, the induced physiological signal is a response to at least one stimulation signal generated by a signal generator, wherein a signal parameter of said stimulation signal is varied.

In one embodiment of the apparatus according to the present invention, the detector is an EEG (electroencephalogram) detector.

In one embodiment of the apparatus according to the present invention the signal parameter is the frequency f of the stimulation signal.

In one embodiment of the apparatus according to the present invention the criterion is a maximum amplitude of the physiological signal wherein the optimal setting of the varied frequency f is formed by a resonance frequency ($f_R$), for example of the EEG-signal. The resonance frequency $f_R$ is that frequency which produces the maximum possible response, for example the maximum possible EEG amplitude.

In one embodiment of the apparatus according to the present invention the resonance frequency $f_R$ is determined by varying the frequency f of the sensory stimulation signal SSS applied to the sensory organ of the person and then selecting that specific frequency which reaches the predetermined criterion.

In one embodiment of the apparatus according to the present invention the sensory stimulation signal SSS is an optical (visual) stimulation signal, an auditory stimulation signal or a mechanical stimulation signal (vibration) to excite the sense of touch on the skin surface.

In one embodiment of the apparatus according to the present invention the resonance frequency $f_R$ is determined by varying the frequency f of an electrical stimulation signal ESS applied to the person automatically within a predetermined frequency range.

In one embodiment of the apparatus according to the present invention the stimulation signal is a sine wave signal.

In one embodiment of the apparatus according to the present invention the stimulation signal is a rectangular signal.

In one embodiment of the apparatus according to the present invention the frequency f of the stimulation signal is varied automatically in a frequency range between 0-100 Hz to determine a resonance frequency $f_R$ of the electroencephalogram signal (EEG).

In one embodiment of the apparatus according to the present invention the determined optimal setting of the signal parameter of the simulation signal is stored in a memory unit.

In one embodiment of the apparatus according to the present invention the control unit is connected to the signal generator via control lines to control said signal generator such that the electrical stimulation signal ESS and the sensory stimulation signals SSS comprise a predetermined phase relationship.

In one embodiment of the apparatus according to the present invention the electrical stimulation signal ESS is applied to the person via electrodes wherein at least one electrode is fixed near the sensory organ of the person or fixed directly to the skull.

In a further embodiment of the apparatus according to the present invention the electrical stimulation signal ESS is applied to the person via magnetic stimulation coils, wherein at least one stimulation coil is fixed near the sensory organ of the person or directly to the skull of the person.

In one embodiment of the apparatus according to the present invention the sensory organ is formed by an eye of the person.

In an alternative embodiment of the apparatus according to the present invention the sensory organ is formed by an ear of the person.

In one embodiment of the apparatus according to the present invention the sensory organ is formed by a touch sensory organ of the person.

In one embodiment of the apparatus according to the present invention the optical sensory stimulation signal is formed by a pulsed flash light generated by a light bulb.

In an alternative embodiment of the apparatus according to the present invention the optical sensory stimulation signal is formed by an optical signal generated by a light emitting diode.

In a further alternative embodiment of the apparatus according to the present invention the optical sensory stimulation signal is formed by a predetermined stimulus pattern displayed on a display monitor.

In one embodiment of the apparatus according to the present invention the optical sensory stimulation signal is applied to an impaired region of the visual field of the eye or the brain.

The invention further provides a method according to claim 25.

The invention provides a method for stimulating a brain of a person comprising the steps of detecting a physiological signal generated by said brain, comparing the detected physiological signal with a pre-selected criterion to determine an optimal setting of a variable signal parameter, and applying an electrical stimulation signal and/or at least one further sensory stimulation signal to a sensory organ, wherein the signal parameter of the stimulation signals are adjusted to the determined optimal setting of said signal parameter.

In the following embodiments of the apparatus and the method according to the present invention are described with reference to the enclosed figures.

Figure 2:
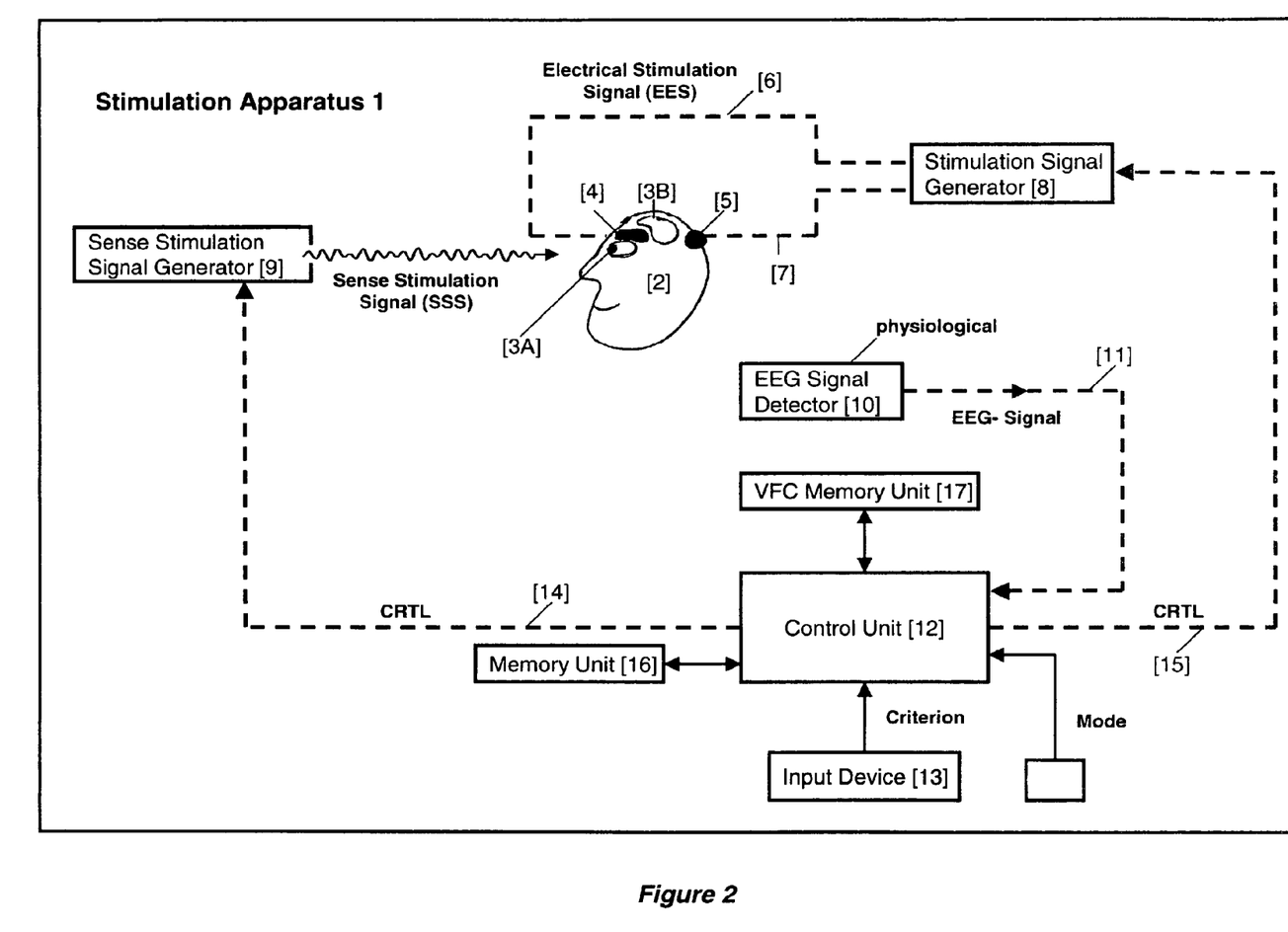
FIG. 2 shows an embodiment of a stimulation apparatus according to the present invention.

As can be seen from FIG. 2 a stimulation apparatus 1 according to an embodiment of the present invention is provided for stimulating a sensory organ 3A of a person 2 wherein in the embodiment shown in FIG. 2, the stimulated sensory organ 3A is formed by an eye of the person 2, wherein each sensory organ 3A stimulates a brain 3B of the person 2

In the embodiment shown in FIG. 2 at least one first electrode 4 is fixed close to or around the eye 3A and a second electrode 5 is fixed to the skull of the person 2 as a reference electrode. Both electrodes 4,5 are connected by signal lines 6,7 to a stimulation signal generator 8 generating an electrical stimulation signal ESS. A further sensory stimulation signal generator 9 is provided for generating a sensory stimulation signal SSS which is formed in the embodiment shown in FIG. 2 by an optical signal.

A signal detector 10 for detecting an induced or spontaneous physiological signal is provided. The signal detector 10 is formed, for instance, by an EEG-detector 10 which detects an electroencephalogram signal EEG by one or more electrodes which are attached to the skull of the person 2. The EEG signal is output via signal line 11 to a control unit 12. The control unit 12 compares the detected electroencephalogram signal with a criterion which is input by an operator via an input device 13. The control unit 12 controls the sensory stimulation signal generator 9 via a control line 14 and the electrical stimulation signal generator 8 via a control line 15. In a first step one of the two signal generators 8, 9 or both signal generators 8, 9 apply a stimulation signal to the person 2, wherein a signal parameter of the respective stimulation signal such as the frequency f of the stimulation signal is varied automatically within a predetermined frequency range $\Delta f$. The control unit 12 monitors the measured electroencephalogram signal generated by the EEG signal detector 10 and compares the detected electroencephalogram signal EEG with the selected criterion to determine an optimal setting of the varied signal parameter.

In other embodiments, the detector 10 detects other physiological signals of the brain 3B such as a magneto-encephalogram signal or a BOLD-signal measured by functional magnetic resonance imaging.

In a possible embodiment the selected criterion is a maximum amplitude of the physiological signal, e.g. the electroencephalogram signal EEG caused by a specific frequency of the applied stimulation signals. In this embodiment the optimal setting of the varied frequency f is formed by a resonance frequency $f_R$ of the detected physiological signal. At the resonance frequency $f_R$, the physiological signal comprises a maximum amplitude $A_{max}$.

In one embodiment the resonance frequency $f_R$ is determined by varying the frequency f of the sensory stimulation signal SSS applied to the sensory organ 3A of the person 2 by the sensory stimulation signal generator 9.

In an alternative embodiment the resonance frequency $f_R$ is determined by varying the frequency f of the electrical stimulation signal ESS generated by the stimulation signal generator 8 within a predetermined frequency range $\Delta f$. Typically, the electrical stimulation signal ESS applied to the head of the person 2 is in the range of 0-100 Hz preferably around 10 Hz and at a current of 0-5.0 mAmp, preferably 0.5 mAmp. The signal of the applied electrical stimulation signal ESS can be formed by rectangular pulses or sine wave pulses. The signal pulses are applied either as single pulses or as pulse trains which consist of many repetitive pulses. Furthermore, the shape of the pulse can vary; for instance, a high amplitude positivity can be followed by a low amplitude but extended negativity. Preferably, the sum of both equals zero.

In the embodiment shown in FIG. 2 the electrical stimulation signal ESS is applied to a skull of the person 2 via electrodes 4,5. One or several electrodes 4 are fixed to the region near the eyeball and the neutral reference electrode 5 is placed on the skull or at the skin of another body part.

In one embodiment of the apparatus according to the present invention the electrodes 4,5 are attached directly to the skull of the person 2.

In an alternative embodiment of the apparatus 1 according to the present invention the electrical stimulation signal ESS is applied to the person 2 by means of magnetic stimulation coils (transcranial magnetic stimulation) which are held in position by a holding device.

While stimulating the sensory organ 3A of the person 2 the EEG-signal detector 10 detects an electroencephalogram signal of the person 2 10 can collect information from one or from more than one recording electrodes In a possible embodiment EEG-electrodes are fixed to the skull of the person and brain-wave-signals are measured preferably as evoked potentials. The frequency f of the applied simulation signal which might be formed by the electrical stimulation signal ESS or by both the electrical and the sensory stimulation signal is varied in a predetermined frequency range $\Delta f$ to determine an optimal setting of the frequency f producing a maximum amplitude $A_{max}$ of the electroencephalogram signal. This optimum frequency forms the resonance frequency $f_R$ which is stored by the control unit 12 as an EEG-parameter in a memory unit 16 of the stimulation apparatus 1. Each individual person 2 has their own individual resonance frequency $f_R$ at a given point in time.

In a first operation mode the stimulation apparatus 1 according to the present invention is switched to a measuring procedure for determining the respective resonance frequency $f_R$ of the person 2. The control unit 12 is switched to this operation mode by the operator by means of mode control switch 17, as shown in FIG. 2. The stimulation apparatus 1 indicates by a display when the resonance frequency $f_R$ of the person 2 has been found and is stored into memory unit 16.

When the resonance frequency $f_R$ of the respective person 2 is found the stimulation apparatus 1 switches in one embodiment automatically to another operation mode wherein the electrical stimulation signal ESS and at least one further sensory stimulation signal SSS are both applied to the sensory organ 3A with a frequency f that is adjusted to the determined optimal setting of the signal parameter, i.e. to the resonance frequency $f_R$ of the person 2 stored in the memory unit 16.

In an alternative embodiment the operator switches the stimulation apparatus 1 to the other operation mode when the resonance frequency $f_R$ has been determined.

In one embodiment the stimulation apparatus 1 first records a spontaneous EEG of the person 2, analyzes the actual alpha brain wave activity and then stimulates with the stimulating electrode 4 a desired frequency based on the spontaneous EEG recording. For example, if a person 2 has a spontaneous EEG alpha activity of 11.0 Hz but the pre-selected frequency target is 10.2 Hz, then the stimulating electrode will be set at 10.2 Hz until the point where the spontaneous EEG show a value closer to 10.2 Hz as well.

In one embodiment of the stimulation apparatus 1 according to the present invention the stimulation apparatus 1 comprises a phase control unit which controls a phase relationship between the sensory stimulation signal SSS and the electrical stimulation signal ESS applied to the person 2.

In one embodiment the sensory stimulation SSS and the electrical stimulation signal ESS are applied simultaneously to the person 2, i.e. a phase difference $\Delta\phi$ between the two signals is zero.

In a possible embodiment the electrical stimulation signal ESS comprises a resonance frequency $f_R$ of 10 Hz and is applied to the person 2 in a synchronous manner with a 10 Hz visual stimulus signal.

In an alternative embodiment there is predetermined phase difference $\Delta\phi$ between the two stimulation signals. For instance an electrical pulse train is applied to the person 2 via electrodes 4,5 for a duration of 10 seconds with a specific frequency and then visual pulses are applied to the sensory organ 3A of the person 2 at the same frequency f for the next 10 seconds.

In yet another embodiment, the current strength of the electrical stimulating electrode 4 is varied while the frequency f is held constant.

In one embodiment the electrical stimulation signal ESS and the sensory stimulation signal SSS are applied in an alternating manner at a predetermined frequency f.

In one embodiment the electroencephalogram EEG signal is measured with a silver chloride electrode or a gold electrode positioned on the skull wherein the EEG-signal recording can be performed with a single electrode or multiple electrodes.

The signal generator 9 generating the sensory stimulation signal SSS is formed in one embodiment by a light pulsed generating a bulb flash light.

In an alternative embodiment the sensory stimulation signal generator 9 generates visual stimulation signals SSS formed by light emitting diodes LEDs.

In a still further embodiment of the stimulation apparatus 1 according to the present invention the sensory stimulation generator 9 for generating a visual stimulation signal is formed by a display displaying a predetermined visual signal pattern. Such a stimulus pattern can be formed by any pattern useful to produce visual perceptions. A possible pattern is a moving spiral displayed to the person 2. The visual stimulus can be any kind of stimulus, e.g. a moving pattern or a simple stationary geometric pattern such as a triangle or a square.

Figure 3:
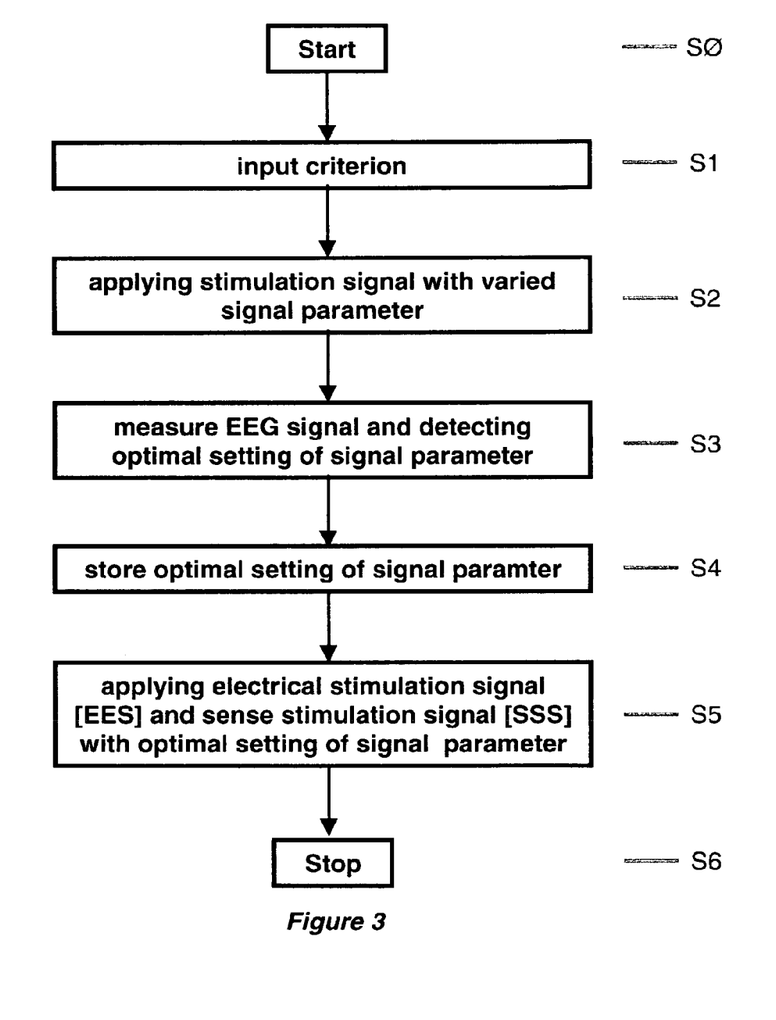
FIG. 3 shows a flow-chart for illustrating a possible embodiment of the method according to the present invention.

FIG. 3 shows a flow chart of possible embodiment of the method according to the present invention.

After starting step S0, the control unit 12 operates for determination of an optimal setting of a variable signal parameter previously set by the input device. The selected criterion can be a resonance frequency or some other physiological parameter such as a brain wave frequency, for example a certain alpha-wave frequency. When the operator has input the criterion in Step S1, the stimulation apparatus 1 switches in one embodiment to a first operation mode for determining the optimal setting of the variable signal parameter. In an alternative embodiment stimulation apparatus 1 does not wait for an input of the criterion but automatically starts its operation by using a preselected criterion.

In step S2, a stimulation signal is applied to the person 2 with a varied signal parameter for instance by changing the frequency f of the stimulation signal in the predetermined frequency range Δf. The stimulation signal can be formed by the electrical stimulation signal ESS or by the sensory stimulation signal SSS or by both signals at the same time. The stimulation signal can vary by frequency or current strength or by a combination of the two.

In a step S3 the detector 10 measures the physiological signal, e.g. a EEG signal, and the control unit 12 determines the optimal setting of the varied signal parameter by analysing the generated physiological signal according to the selected criterion.

As soon as the control unit 12 has found the optimal setting of the signal parameter, e.g. the resonance frequency $f_R$ of the person 2 this signal parameter is stored in the memory unit 16 in step S4 and the stimulation apparatus 1 switches automatically to another operation mode for restoring impaired regions of the sensory organ 3A. In this operation mode the stimulation apparatus 1 applies the electrical stimulation signal ESS and the sensory stimulation signal SSS with the optimal setting of the signal parameter, i.e. with the setting stored in the memory unit 16. Both signals ESS, SSS are applied to the person 2 with a predetermined phase relationship.

The duration of the application of the electrical stimulation signal ESS and the sensory stimulation signal SSS corresponds to a predetermined time span of, for instance, several minutes.

Figure 4:
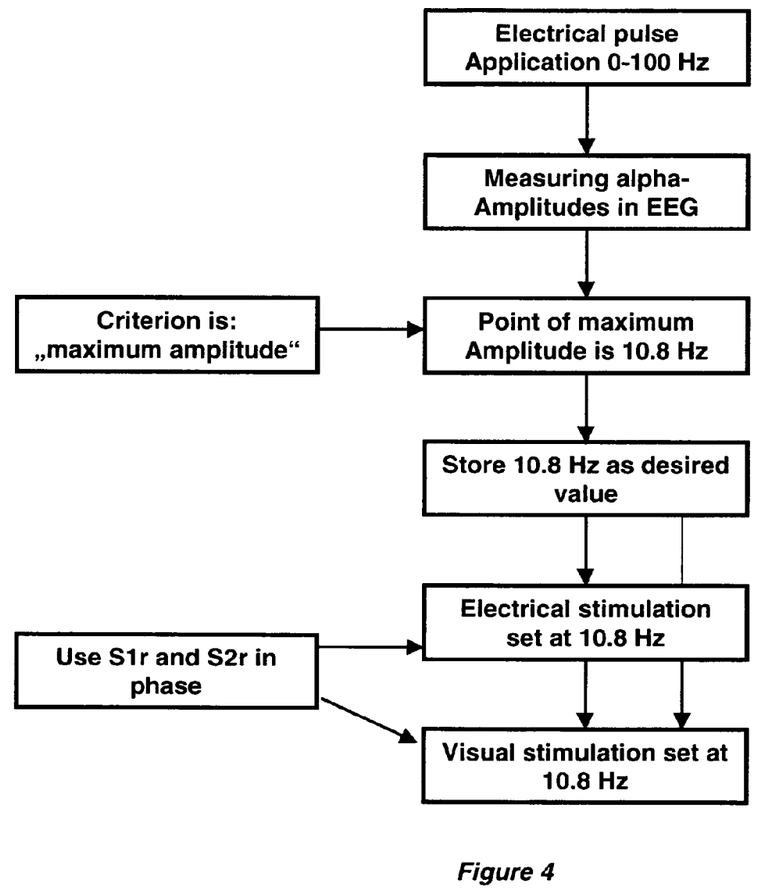
FIG. 4 shows a further flow-chart for illustrating a possible embodiment of the method according to the present invention.

As can be seen from FIG. 4, in one embodiment of the apparatus 1 according to the present invention, first, an electrical pulse signal is applied in a predetermined frequency range of, for example 0 to 100 Hz.

In a further step, alpha amplitudes of the physiological signal are measured by an EEG-detector 10. The operator inputs as a predetermined criterion a maximum amplitude of the measured physiological signal, wherein in the example of FIG. 4, the point of the maximum amplitude is measured at a frequency of 10.8 Hz. This signal parameter, i.e. a frequency of 10.8 Hz is stored in the memory unit 16 of the stimulation apparatus 1 according to the present invention as shown in FIG. 2. In the example of FIG. 4, the operator selects stimulation signals to be applied to the person 2. In the given example, as a first sensory stimulation signal SSS visual stimulation signal is selected and, as a second stimulation signal an electrical stimulation signal ESS is selected to be applied to the person 2 via electrodes. In a further step, an electrical stimulation of the brain 3B is performed by means of the electrical stimulation signal ESS applied to the person 2 via electrodes 4, 5. In a predetermined phase relationship as input by the operator, the visual stimulation of the sensory organ 3A is performed at a frequency of 10.8 Hz being the resonance frequency $f_R$ Of the person at this time point.

The electrical stimulation signal ESS and the visual sensory stimulation signal SSS are coupled to each other. Both signals have a predetermined phase relationship and they are applied to the person 2 at the same frequency f of 10.8 Hz. This signal parameter is detected by evaluating the physiological EEG-signal according to a predetermined objective criterion input by the operator via the input device 13.

Figure 5:
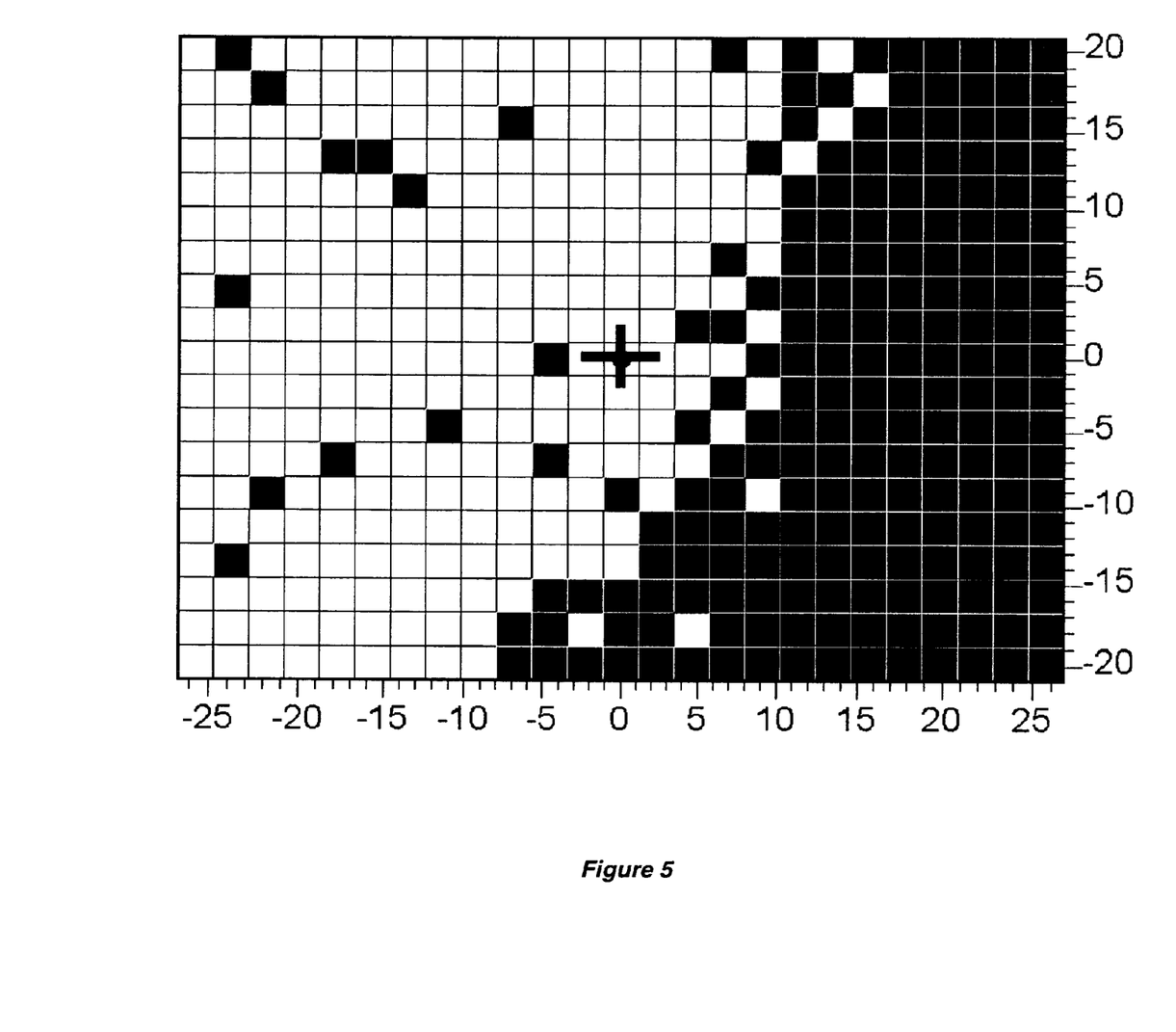
FIG. 5 shows an example for a visual field defect VFD of a person.

FIG. 5 shows an example for a visual field defect chart VFC of an eye of a person 2 comprising blind regions indicated in black. To determine such a visual field defect chart, a simulation signal is presented to a person 2 by means of a monitor and the patient has to fixate his eyes at a cross shown in the center of FIG. 5. Stimulation signals are presented at random positions on the monitor and the patient 2 responds to each stimulus by pressing a key or a response button. When the patient does not react this position is stored in the memory as well and subsequent visual field defect charts which document the patients performance this position is represented by a black square in the visual field defect chart VFC as shown in FIG. 5. If a patient reacts properly a white square is accorded to the respective area. The visual field defect chart VFC reveals regions of vision versus areas of blindness.

In most cases patients do not only comprise areas of vision and areas of blindness but also areas of residual vision which are partially damaged, i.e. the patient sometimes responds to a stimulation signal applied for this area and sometimes he does not.

Figure 6A:
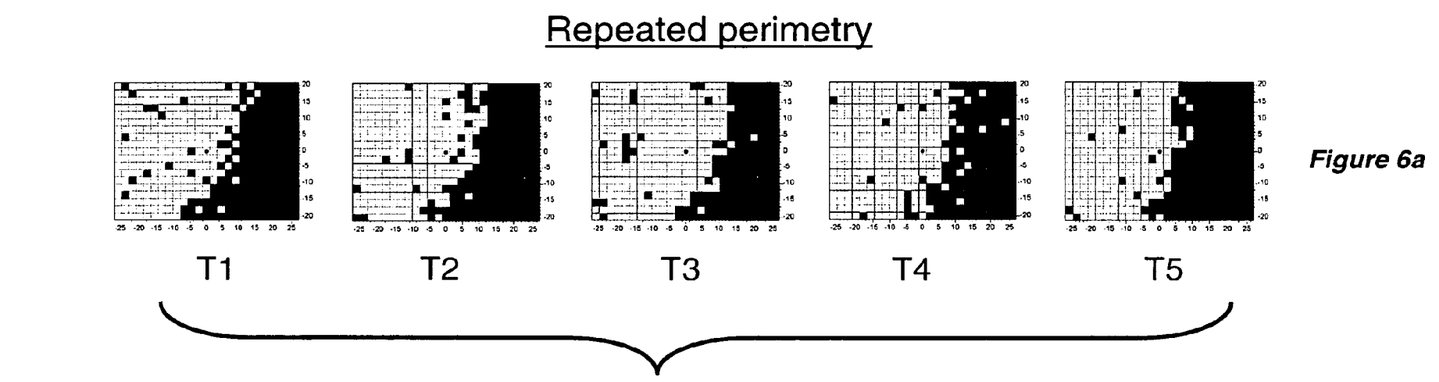
FIGS. 6a, 6b shows an example for the determination of areas of impaired vision of a person.
Figure 6B:
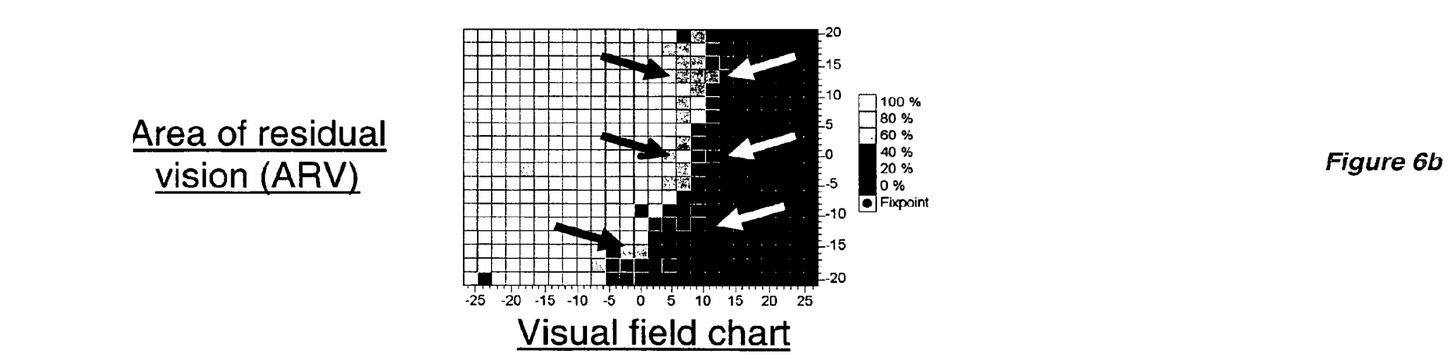

FIG. 6 shows a process of how such areas of residual vision are determined. At various times T1-TX separate visual field defect charts are generated and, subsequently, a super-imposed visual field defect chart VFC is generated as shown in FIG. 6b. This parametric testing reveals areas where the patient 2 responds unreliable to vision stimuli shown as grey areas in FIG. 6b.

In a preferred embodiment of the stimulation apparatus 1 according to the present invention the visual stimulation signal SSS is applied only to damaged areas, i.e. areas of residual vision (grey regions in FIG. 6b) and areas of blindness (black regions in 6b).

Figure 7A:
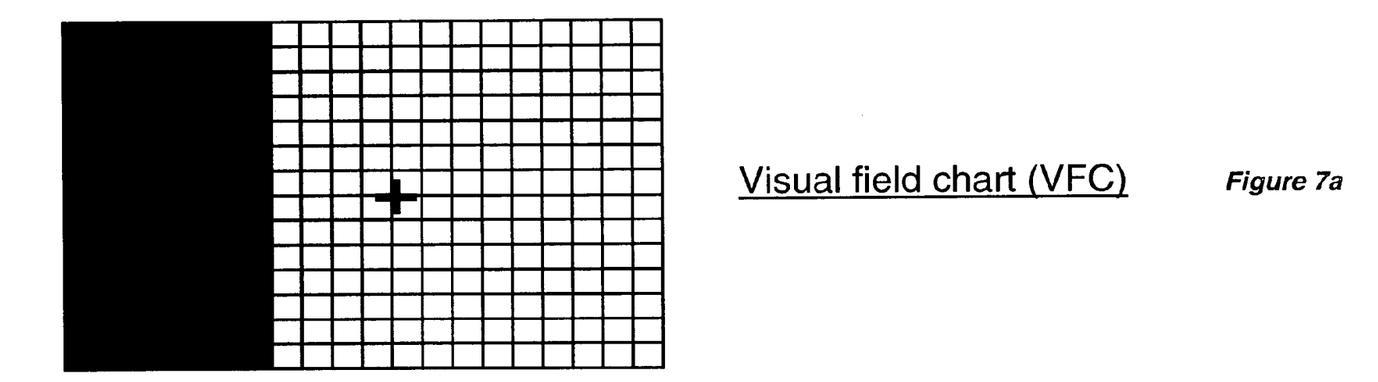
FIGS. 7a, 7b show an example for a visual field defect chart and a corresponding signal pattern as employed by an embodiment of the apparatus according to the present invention.
Figure 7B:
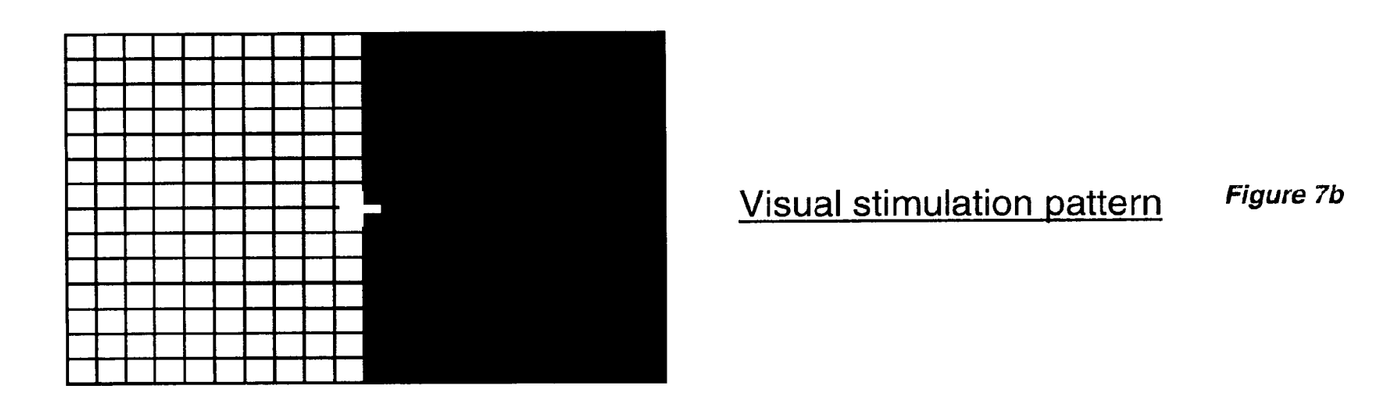

FIG. 7a shows a parametric visual field defect chart VFC of a patient 2. FIG. 7b shows the regions where a stimulation signal SSS is presented to the patient 2 having the visual field defect chart of FIG. 7a. The white areas in FIG. 7b indicate areas of maximum stimulation, grey indicates intermediate stimulation and black areas indicate areas of no stimulation. As can be seen from FIGS. 7a, 7b blind areas of FIG. 7a receive maximum stimulation as shown in FIG. 7b.

In a preferred embodiment the greater the deficit of a region of the eye indicated by the visual field defect chart VFC the greater the amount of visual stimulation for this region.

In one embodiment the amount of visual stimulation is increased by increasing the frequency f of the sensory stimulation signal SSS.

In an alternative embodiment the amount of visual stimulation is increased by increasing the amplitude of the sensory stimulation signal SSS.

In a preferred embodiment of the stimulation apparatus 1, a control unit 12 is connected to a visual field defect chart memory 17 storing the visual field defect chart VFC of the respective person 2.

The visual field defect chart VFC of the person 2 is loaded to the memory 17 in one embodiment via an interface from a data-carrier.

In an alternative embodiment stimulation signal generator 9 formed by a monitor or a display is provided for performing a perimetric method to create the visual field defect chart VFC of the person 2.

In this embodiment, the simulation apparatus 1 is used in a first operation phase to create a visual field defect chart VFC of the person 2. Then in a second operation phase, the resonance frequency $f_R$ of the person 2 is determined and in a third phase the sensory organ 3A of the person 2 is stimulated by the stimulation signals wherein the amount of stimulation, i.e. the amplitude or frequency, is adjusted in response to the visual field defect chart VFC of the person 2 stored in the memory unit 16. Accordingly, in this embodiment of the stimulation apparatus 1, a first signal parameter of the stimulation signals SSS, ESS e.g. the frequency f of the stimulation signal is adjusted to the optimal setting, i.e. to the resonance frequency $f_R$ of the person 2, and another signal parameter of the stimulation signals SSS, ESS, e.g. the amplitude is adjusted depending to the VFC visual field defect chart of the person 2 stored in the VFC chart memory 17.

The restoration stimuli signals can be presented from several seconds to a longer time period such as an hour.

Figure 8A:
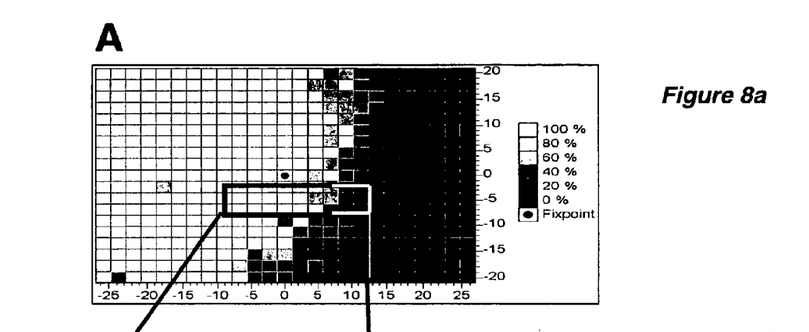
FIGS. 8a to 8d show a visual field defect chart VFC and examples for stimulation signals applied to the sensory organ by the apparatus according to the present invention.
Figure 8B:
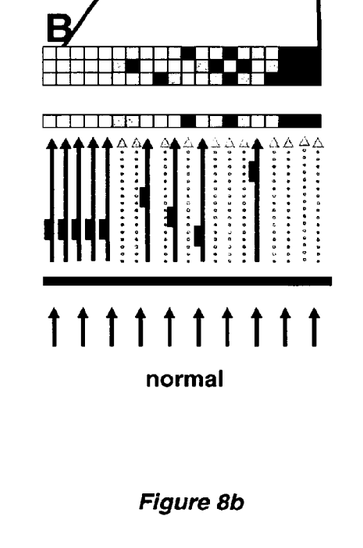
Figure 8C:
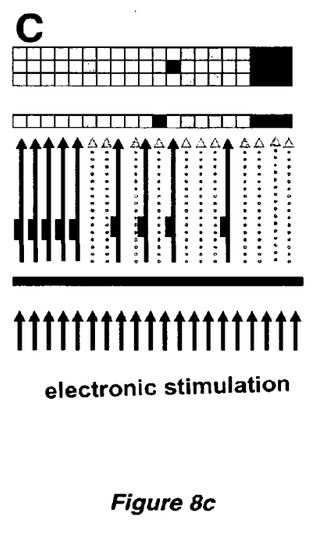
Figure 8D:
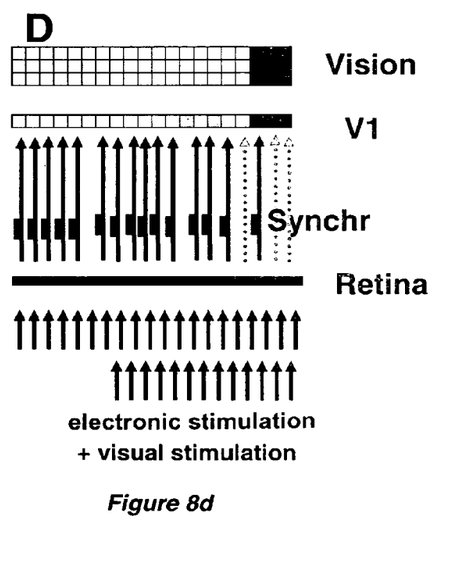

FIG. 8b-8d show an example of an application stimulation signal to an eye 3A of a person 2 having a visual field defect chart VFC as shown in FIG. 8a. The visual field defect chart VFC shows different regions of the eye showing different degrees of vision. For example, undamaged regions show an ability of 100 percent (white) and completely blind regions show an ability of 0 percent (black). Grey regions in the visual field defect chart VFC indicate the presence of residual vision of some surviving neurones. Cells in these residual regions which are partially damaged areas of the brain, fire in an asynchronous manner (FIG. 8b). During electro-stimulation as shown in FIG. 8c the residual neurones are activated repetitively at the same time and the evoked potential causes phosphenes. By repetitive stimulation of these areas, the residual vision can be enhanced significantly. This can be seen in FIG. 8b where cells in the damaged areas do not fire in synchronous manner. By application of an electrical simulation signal ESS, the cells fire synchronously to each other. When the electrical stimulation signal ESS and the visual stimulation signal SSS are coupled to each other as shown in FIG. 8d more cells are expected to fire which will then produce a more intense restoration effect in the brain.

In an embodiment of the stimulation apparatus 1 according to the present invention, the apparatus sends stimulation signals SSS as an optical sensory stimulation signal generated by an optical signal generator such as a light bulb.

In an alternative embodiment stimulation apparatus 1 according to the present invention, the apparatus 1 is provided for stimulating an auditory organ 3A of a person 2, i.e. an ear of the person 2. In this embodiment, the stimulation signal SSS provided by the sensory stimulation signal generator 9 is an auditory stimulus such as a pulsed tone or click which is systematically sent with different frequencies (pitch) or loudness (in decibel). These stimulation signals can be presented at random or in a particular order, e.g. ascending frequencies.

The stimulation apparatus 1 identifies, in a possible embodiment, auditory deficits on the basis of a criterion to determine parameters of an auditory restoration stimulation signal. For example, a tone of x decibel is presented to the person 2 in a frequency range 0-100 Hz. If the patient does not respond for instance at frequencies ranging from 20-40 Hz at a given loudness, the sensory stimulation signal SSS and the electrical stimulation signal ESS are applied to the patient 2 at this frequency f at the same time or with a predetermined phase difference.

In a still further embodiment of the stimulation apparatus 1 the apparatus 1 is used for stimulation of somatosensory organs i.e. a touching sensory of the person 2. In this embodiment, the sensory stimulation signal generator 9 is formed by a vibration device placed on the skin of the person 2. A vibration frequency is systematically varied and with different pressure on the skin. The frequency f of the vibration device is varied at random or in a particular order, for example, by increasing the vibration frequency. In this manner the simulation apparatus 1 identifies somatosensory deficits. For example, a vibration signal can be presented in a frequency range $\Delta f$ from 0-100 Hz and then a stimulation signal SSS is selected having a frequency which corresponds to the deficient frequency.

In a possible embodiment the deficiencies of the ear or the touch sense is detected automatically by the control unit 12 by evaluating a physiological signal detected by the detector 10.

In possible embodiments, memories are provided for storing a chart of the deficiencies of the respective sensory organ 3A, which can be formed by an ear or by a skin area of the person 2. An acoustic chart of the patient's ear or a somatosensory chart of the skin body portion of the patient is stored in a memory indicating the frequencies of impaired hearing or impaired feeling.

The present invention is useful not only for the treatment of sensory disorders (such as vision loss, hearing loss or somatosensory loss) but for other disorders as well because synchrony of brain waves (EEG) as induced by electro-stimulation with or without sensory coupling may affect all disorders where the nervous system is impaired. These disorders comprise: Stroke and head injury, Coma and loss of consciousness; neglect, cognitive impairments and dementia after Alzheimer's Disease; cognitive impairments in normal aging; Parkinson's Disease, movement disorders as induced by, for example, hemiplegia; Speech disorders, including Aphasia; Memory impairments; deficits in attention and concentration, Multiple Sclerosis, Huntington's Disease, reading impairments including dyslexia, Vision impairments affecting the optic system and the retina including myopia, glaucoma, macular degeneration, strabismus, amblyopia, retinitis pigmentosa developmental disorders in children; peripheral nerve disorders.

The invention claimed is:

1. A stimulation apparatus for stimulating a brain of a person comprising:
   (i) a first signal generator configured to apply a generated electrical stimulation signal to a sensory organ of said person;
   (ii) a second signal generator configured to apply a generated sensory stimulation signal to the sensory organ of said person;
   (iii) a signal detector configured to detect an induced brain signal, wherein the induced brain signal is an electro- or magnetoencephalogram signal generated by the brain of said person in response to the applied electrical stimulation signal or in response to the electrical stimulation signal and the sensory stimulation signal; and (iv) a control unit which is (a) configured to control the first signal generator, (b) configured to control the second signal generator and (c) configured to receive and analyze the induced brain signal from the signal detector, wherein, in a first operation mode, the control unit is configured to vary a frequency of the applied stimulation signal formed by the electrical stimulation signal or by both, the electrical and the sensory stimulation signal over a predetermined frequency range while analyzing the induced brain signal to determine an optimal setting of the frequency producing a maximum amplitude of the induced brain signal, wherein, in a second operation mode, the control unit is configured to apply both the electrical stimulation signal and the sensory stimulation signal to the sensory organ with a frequency that is adjusted to the determined optimal setting of the frequency forming an individual resonance frequency of said person, wherein the control unit further includes a phase control unit, the phase control unit controlling a phase relationship between the sensory stimulation signal generated by the second signal generator and the electrical stimulation signal generated by the first signal generator, wherein the electrical stimulation signal generated by the first signal generator and the sensory stimulation signal generated by the second signal generator have a predetermined phase relationship, wherein each of the sensory stimulation signal and the electrical stimulation signal has a frequency associated therewith, and wherein the frequency of the sensory stimulation signal generated by the second signal generator is equal to the frequency of the electrical stimulation signal generated by the first signal generator.

2. The stimulation apparatus according to claim 1, wherein said signal detector is an EEG-detector.

3. The stimulation apparatus according to claim 2, wherein said sensory stimulation signal is an optical stimulation signal, an auditory stimulation signal, or a vibration stimulation signal.

4. The stimulation apparatus according to claim 3, further comprising a light bulb, wherein the optical sensory stimulation signal is formed by pulsed flash light generated by said light bulb.

5. The stimulation apparatus according to claim 3, further comprising a light emitting diode, wherein the optical sensory stimulation signal is generated by said light emitting diode device.

6. The stimulation apparatus according to claim 3, further comprising a display monitor, wherein the optical sensory stimulation signal is formed by a predetermined stimulus pattern displayed on said display monitor.

7. The stimulation apparatus according to claim 1, wherein said stimulation signal is a sine wave signal or a rectangular signal.

8. The stimulation apparatus according to claim 1, wherein the frequency of the stimulation signal produced by the first signal generator or the second signal generator is varied in a frequency range $\Delta f$ of about 0-100 Hz.

9. The stimulation apparatus according to claim 1, further comprising a memory unit, wherein the determined optimal setting of the frequency of the stimulation signal is stored in said memory unit.

10. The stimulation apparatus according to claim 1, further comprising control lines, wherein said control unit is connected to the signal generators via said control lines to control said signal generators such that the electrical stimulation signal and the sensory stimulation signal comprise a predetermined phase relationship.

11. The stimulation apparatus according to claim 1, further comprising at least one of electrodes and magnetic stimulation coils, wherein the electrical stimulation signal is adapted to be applied to said person via said electrodes or magnetic stimulation coils, and wherein at least one of said electrodes or magnetic stimulation coils is adapted to be fixed near the sensory organ of said person.

12. The stimulation apparatus according to claim 11, wherein the sensory organ to which said electrode or magnetic stimulation coil is adapted to be fixed is formed by an eye of said person, by an ear of said person or by a touch sensory organ of said person.

13. The apparatus according to claim 12, wherein the optical sensory stimulation signal is adapted to be applied to an impaired region of the eye of said person.

14. The stimulation apparatus according to claim 1, wherein a memory is provided for storing a sensitivity chart indicating a sensitivity of areas of the sensory organ to a respective sensory stimulation signal.

15. The method stimulation apparatus according to claim 1, wherein a spontaneous electroencephalogram (EEG) signal of the person is recorded;

wherein the frequency of the actual alpha brain wave activity of the person is analyzed; and wherein the electrical stimulation signal used to stimulate the sensory organ of the person is based on the recorded spontaneous electroencephalogram (EEG) signal.

* * * * *